United States Patent [19]

Tutrone, Jr.

[11] Patent Number: 5,603,685
[45] Date of Patent: Feb. 18, 1997

[54] INFLATABLE VAGINAL PESSARY

[76] Inventor: Donald F. Tutrone, Jr., 3 Wendover Rd., Baltimore, Md. 21218

[21] Appl. No.: 434,362

[22] Filed: May 5, 1995

Related U.S. Application Data

[63] Continuation of Ser. No. 273,391, Jul. 1, 1994, abandoned.

[51] Int. Cl.⁶ ............................................ A61F 2/00
[52] U.S. Cl. ...................... 600/29; 128/836; 128/885
[58] Field of Search .................................. 128/830, 834, 128/836, 841, 885, 897, 898, DIG. 25; 600/29–31; 623/11

[56] References Cited

U.S. PATENT DOCUMENTS

| | | | |
|---|---|---|---|
| 2,638,093 | 5/1953 | Kulick | 128/DIG. 25 X |
| 3,646,929 | 3/1972 | Bonnar | |
| 3,797,478 | 3/1974 | Walsh et al. | 600/29 |
| 3,841,304 | 10/1974 | Jones | 128/DIG. 25 X |
| 4,946,449 | 8/1990 | Davis, Jr. | 128/DIG. 25 X |
| 4,981,470 | 1/1991 | Bombeck | 128/635 |
| 5,007,894 | 4/1991 | Enhorning | |
| 5,041,077 | 8/1991 | Kulick | 128/DIG. 25 X |
| 5,224,494 | 7/1993 | Enhorning | |
| 5,306,226 | 4/1994 | Salama | 128/DIG. 25 X |

OTHER PUBLICATIONS

UroMed Corporation Common Stock Prospectus, PailWebber Incorporated, Vector Securities International, Inc., Jan. 1994.

*Primary Examiner*—Angela D. Sykes
*Assistant Examiner*—Samuel Gilbert
*Attorney, Agent, or Firm*—Cooley Godward Castro Huddleson & Tatum

[57] ABSTRACT

A pessary device, comprising a first inflatable chamber adapted to fit in the vestibule of the vaginal cavity of a human when inflated, wherein the chamber compresses the urethra of the human when inflated; an anchor member adapted to snugly fit in the vaginal cavity, the anchor member being connected to the inflatable chamber on the posterior side of the chamber when the pessary is in its normal operating position; and an inflation tube having a first end fluidly connected to the inflatable chamber and a second end connected to an inflation valve located external to the vagina when the pessary device is in its normal operating position that permits inflation and deflation of the inflatable chamber without disturbing the fit of the anchor member.

19 Claims, 3 Drawing Sheets

INFLATABLE VAGINAL PESSARY

CROSS REFERENCE TO RELATED APPLICATIONS

This application is a continuation of U.S. application Ser. No. 08/273,391, filed Jul. 1, 1994, now abandoned.

TECHNICAL FIELD

The present invention relates to an inflatable vaginal pessary suitable for treating urinary incontinence, cystoceles, rectoceles, and uterine prolapse.

BACKGROUND

Continence, or normal control of urine retention in the bladder, involves the coordination of the bladder, bladder neck and urinary sphincter. The body stores urine in the bladder by maintaining a closed bladder neck and a contracted urinary sphincter muscle. To pass urine the bladder contracts while the bladder neck opens and the urinary sphincter muscle relaxes.

Urinary incontinence (UI) occurs when one or more of the anatomical structures related to urine storage malfunctions and leads to a loss of control of urination. The most common type of incontinence is caused by hypermobility of the bladder neck and urethra due to a weakening of the tissues surrounding these structures. In females, pelvic trauma associated with child birth is a common cause of tissue weakening. Another cause of incontinence is a deficiency in urinary sphincter muscle control, intrinsic sphincter deficiency (ISD). It is estimated that approximately 8.5 million women suffer from UI in the United States. Up to 75% of female nursing home patients experience some degree of urinary incontinence, creating a tremendous economic, as well as hygienic, burden.

Female incontinence is currently treated using devices, surgical techniques, behavioral techniques and pharmaceuticals. Devices used to treat female incontinence include absorbent pads, in-dwelling or Foley catheters, vaginal pessaries (U.S. Pat. Nos. 5,224,494, 5,007,894, 4,139,006, 3,554,184, and 3,554,184), solid continence rings (such as the Cook™ or Suarez continence rings), injected or implanted materials (such as Contigen™, based on collagen), the American Medical Services inflatable 800 artificial urinary sphincter, and inflatable urethral plugs (such as Reliance™). Surgery to correct hypermobility of the urethra and bladder neck, behavioral therapy, and drugs that act on bladder neuronal control are also used to combat female incontinence.

The currently available inflatable vaginal pessaries for female incontinence do not sufficiently control incontinence in a comfortable, convenient fashion. U.S. Pat. Nos. 5,007,894 and 5,224,494 disclose inflatable donut-shaped devices. The donut-shaped device of U.S. Pat. No. 5,007,894 when inflated in the vagina transmits intra-abdominal pressure during a stress condition, such as coughing, to the upper urethra. The device has two projections on the donut shaped body to position the device on either side of the urethra in the vaginal cavity. When the donut is inflated it remains in place along the vaginal wall and is deflated for removal. The device of U.S. Pat. No. 5,224,494 is a similarly shaped donut with an additional, long, retractable inflation robe that does not protrude outside the body cavity. The device of U.S. Pat. No. 3,646,929 is an inflatable diaphragm coupled to an elongated solid support that is inserted into the vagina. These devices are difficult to insert into the vagina, uncomfortable to wear, and not likely to stay in place; furthermore they inadequately prevent incontinence or leakage of urine.

Weakening of the pelvic tissues can also result in prolapse of the uterus, bladder, rectum, or intestines. Vaginal pessaries can be used as a mechanical barrier to prevent the extrusion of these organs through the introitus. Devices such as those discussed above can be used to treat prolapses but suffer from many of the drawbacks as discussed for incontinence.

OBJECTS OF THE INVENTION

One object of the present invention is an inflatable vaginal pessary that controls female incontinence more conveniently and comfortably than previous incontinence devices.

Another object of the invention is a vaginal pessary that need not be removed in order for the user to urinate; instead urination is controlled by easily operable valves that regulate the inflation level and pressure of the pessary.

A further object of the invention is a vaginal pessary that remains anchored in the vaginal cavity during movement, such as coughing or exercise, and urination.

Still another object of the present invention is a vaginal pessary that permits the user to control separately (1) the degree of anchoring or snugness of fit of the pessary in the vaginal cavity and (2) the ability to urinate.

Another object of the invention is a vaginal pessary that maintains sufficient stiffness when deflated so that it is easily inserted into the vaginal cavity, similar to a tampon.

A further object of the invention is to provide different embodiments of a vaginal pessary, both one that can remain in place for days and one that is disposable.

A still further object of the invention is a vaginal pessary that can be used to treat cystoceles, rectoceles, uterine prolapse or vaginal prolapse.

SUMMARY OF THE INVENTION

The objects of the invention, both those noted above and other objects that will be apparent in the following detailed description of the invention, have been accomplished by providing a pessary device comprising a plurality of separately inflatable chambers adapted to snugly fit in a vaginal cavity when inflated. The vaginal pessary is made of multiple inflatable chambers adapted to snugly fit in a vaginal cavity when inflated. Inflatable chambers can be either empty when collapsed or can contain an expandable material that assists inflation. At least one chamber is an inflatable chamber that compresses the urethra when inflated. The compression produced by the device reduces the cross sectional area of the urethra lumen. Preferably, the device exerts sufficient pressure against the tissues surrounding the urethra to compress the urethra lumen to the point where no urine leaks out during movement. Inflation of at least one chamber is controlled by an inflation valve or valves fluidly connected to the chamber, typically via a central inflation channel. One valve separately controls deflation and inflation of at least one inflatable chamber during removal and insertion of the device; the same or a different valve controls inflation of a chamber that controls urination. Urination does not require removal of the pessary because the chamber that controls urethra compression is separately operated and inflated from the posterior chamber (or chambers) that controls the anchoring of the device in the vaginal cavity. In another embodiment a non-inflatable posterior member, such as a diaphragm, replaces the posterior chamber used for anchoring. The device can also be used to treat cystoceles, rectoceles, uterine prolapse or vaginal prolapse in a female human by inserting device into the vagina and inflating at least one chamber to prevent tissue intrusion into the vagina.

Another aspect of this invention is a kit for a pessary comprising a valved pessary with a separate fluid pump compatible with the valves on the pessary. Incontinence can be treated by inserting the pessary into the vagina and using the separate pump to inflate at least one chamber sufficiently to compress the urethra and prevent the flow of urine.

The vaginal pessary of the invention is easy to insert and remove from the vaginal cavity, because of its inflatable nature.

DESCRIPTION OF SPECIFIC EMBODIMENTS

Figure 1:
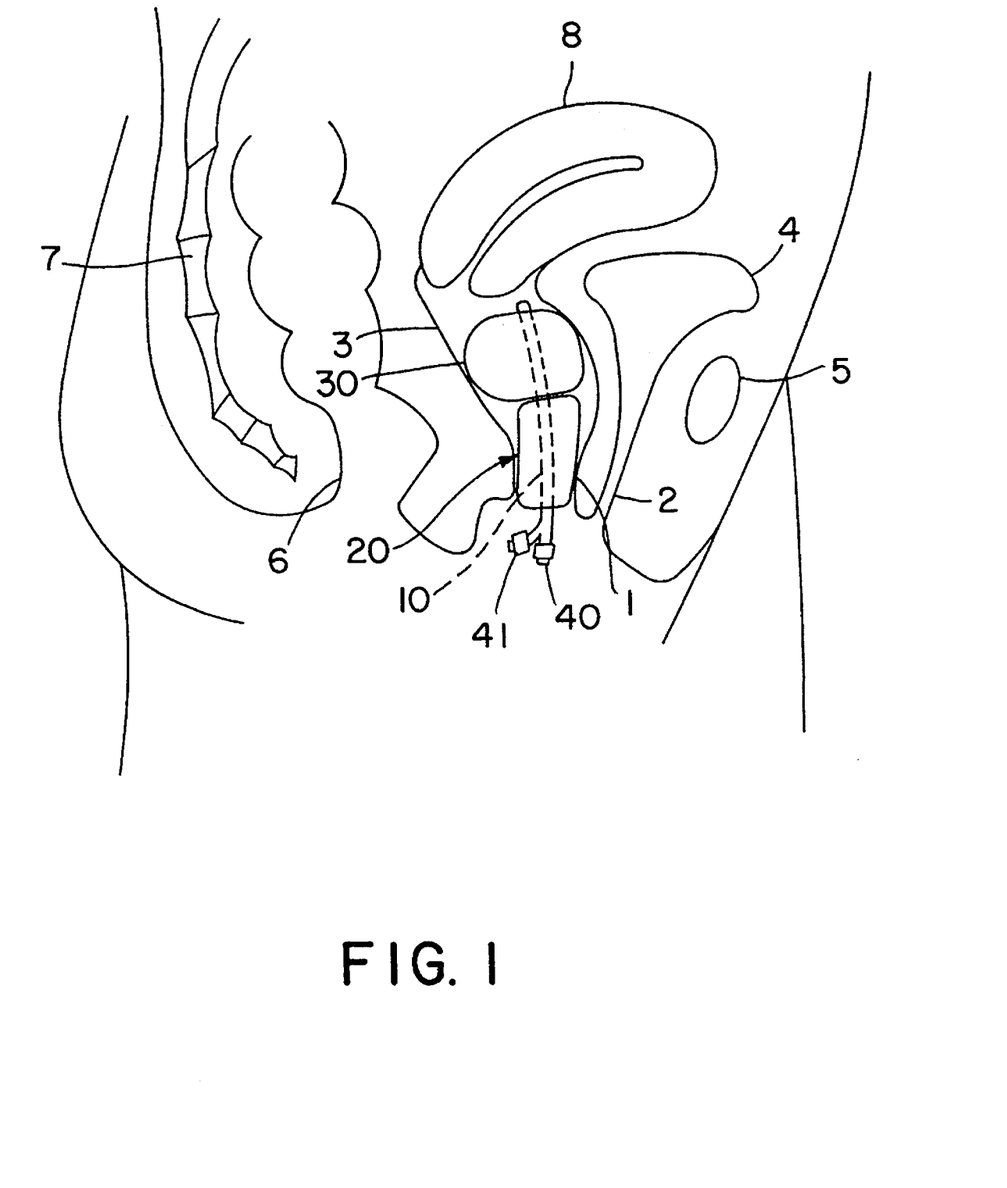
FIG. 1 is a sagittal view of a body cavity showing a vagina with a vaginal pessary of the invention inflated in the vagina.

The invention is most easily understood by considering an embodiment of the invention in relation to the anatomy of the vagina and urinary tract as shown in FIG. 1. The device is generally inserted into the vagina while partially deflated or deflated. Insertion is similar to that for a tampon. Once inside the vagina the device is inflated to secure the device with a snug fit against the walls of the vagina and to compress the urethra. FIG. 1 shows an inflated, two-chambered, first embodiment of the invention with an anterior chamber 20 that snugly fits into the vestibule 1 (anterior region of the vagina) to compress the urethra 2 when inflated and a posterior chamber 30 that snugly fits into the fornix 3 (posterior region of the vagina) when inserted and inflated. In this embodiment an inflation channel 10 provides separate, fluid connections to each chamber so that each chamber can be separately inflated. A first inflation valve 40 fluidly connects the anterior chamber 20 to the atmosphere or a fluid pump. A second inflation valve 41 fluidly connects the posterior chamber to the atmosphere or a fluid pump. Also shown in FIG. 1 are various structures of the pelvic region, including the bladder 4, pubic bone 5, rectum 6, coccyx 7 and uterus 8, in order to show the positioning of the pessary in its normal operating position relative to the organs of the body.

The inflatable vaginal pessary of the invention can be used to treat medical conditions related to the weakening of pelvic tissues, such as, but not limited to, incontinence, cystoceles, rectoceles, uterine prolapse and vaginal prolapse. Generally, the vaginal pessary is made of a plurality of inflatable chambers adapted to snugly fit in a vaginal cavity when inflated. At least one chamber is an anterior chamber (located anteriorly in the vagina) and acts to compress the urethra when inflated. At least one additional chamber, or in the alternative a non-inflatable anchoring member, is a posterior chamber or member (i.e., located posteriorly in the vagina) used to secure or anchor the device in the vagina when inflated or inserted. Inflatable chambers can be empty when compressed or can contain an expandable material (e.g., an elastic foam) to assist expansion. Expandable materials include but are not limited to polyurethane foam, polymeric elastomers and natural fibers. Usually all inflatable chambers are fluidly connected to a valve that controls access to the atmosphere or a fluid pump. However, this is not necessary to practice the invention when a slowly expandable material is used to inflate the posterior chamber. If an expandable material is used inside the chamber, the material is compressed when the device is being inserted into the vagina. Once inside the vagina the expandable material expands to snugly fit the inflatable chamber inside the vagina. A chamber containing an expandable material is considered to be "inflatable" as this word is used to describe the present invention. If the expandable material tends to expand rapidly when pressure is released, it is preferred to control access of air to the chamber containing the expandable material with a valve for better control of expansion. The valve is open while air is being expelled and the chamber compressed, closed to prevent expansion while the pessary is being inserted, and then opened again to allow expansion of the chamber.

Chambers filled with expandable materials do not require a pump for inflation. Empty chambers are filled using a pump to inject a fluid (usually air or water) into the chamber. The pump can either be built into the pessary or can be separate and adapted for connection to the pessary via the valve that controls inflation. Such pumps are discussed below in more detail.

Multiple chambers can be used in place of either the anterior or posterior chamber of the two-chamber device shown in the first embodiment to either compress the urethra or to anchor the device in the vagina or both. As used in this specification, a single "chamber" is an interior space that can be separately inflated and deflated. A single chamber can have internal walls or baffles, but such a chamber is still "single" if it can be inflated through a single valve. If multiple chambers are used to compress the urethra, the shape and total volume of the set of anterior chambers will usually correspond to the shape and total volume of the anterior chamber used individually in a two-chamber device as shown in FIG. 1. Similarly, if multiple chambers are used to function as an anchor, the shape and total volume of the set of anchor chambers will usually correspond to the shape and volume of the anchor chamber used individually in a two-chamber device. Two-chamber devices are preferred for their ease of operation.

Figure 3:
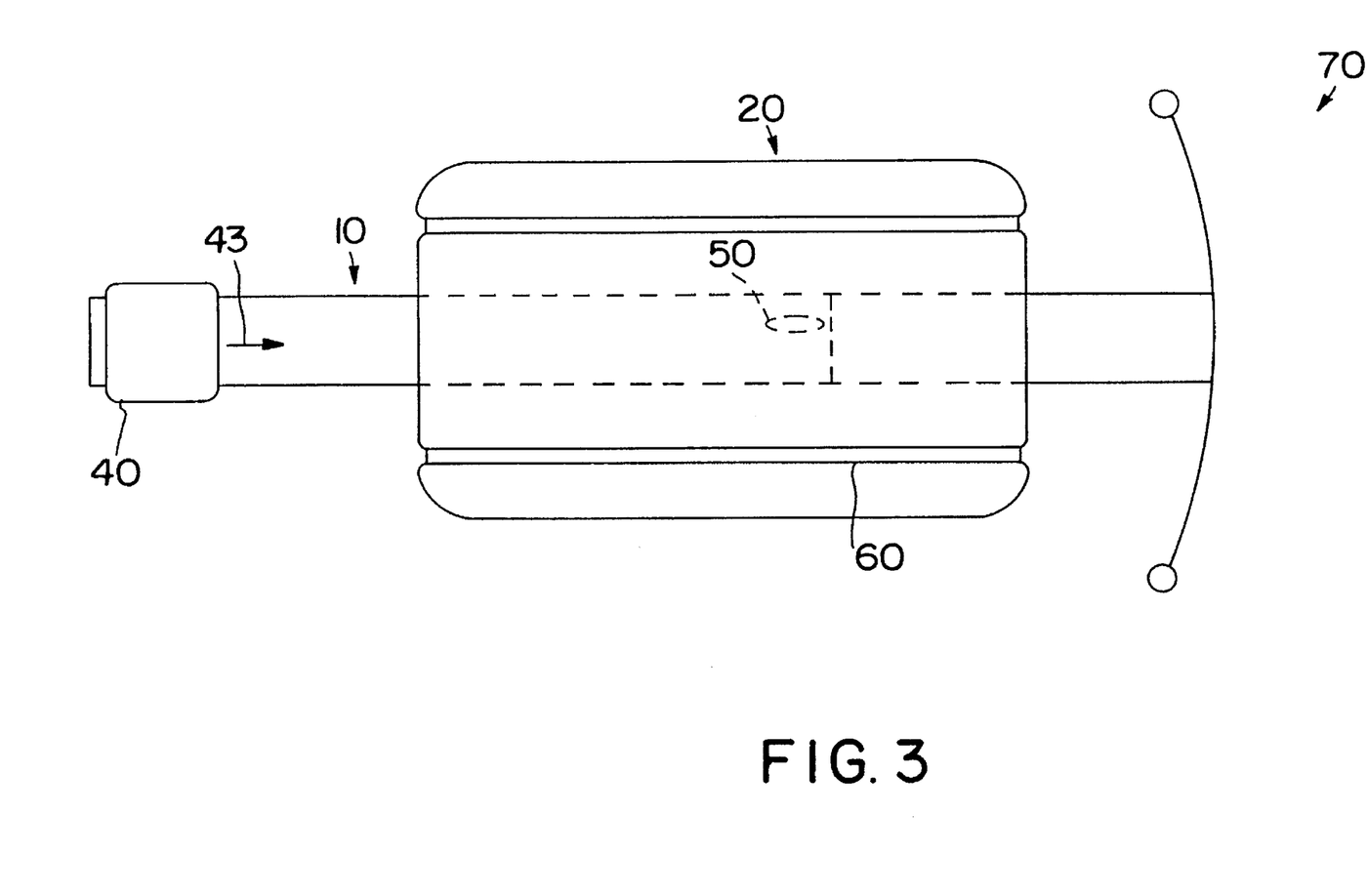
FIG. 3 is a plan view of a second embodiment of the vaginal pessary having an inflatable chamber and a non-inflatable posterior member.

In another embodiment of the invention, only one chamber, the anterior chamber, is inflatable, and the device is secured in the posterior region of the vagina by a non-inflatable posterior member. In this embodiment the posterior member is preferably adapted in the shape of a contraceptive diaphragm to snugly fit in the fornix. Generally, a circular shaped diaphragm 60 will be used. The inflation channel or another central member that provides rigidity for insertion of the pessary, as discussed below, preferably attaches in the center of the diaphragm in this embodiment.

Each inflatable chamber of the pessary is adapted to snugly fit in the vagina when inflated in its normal operating position. When inflated, the anterior chamber presses against the walls of the vagina with sufficient pressure to compress the urethra. When inflated, the posterior chamber presses against the vaginal walls with sufficient pressure to prevent accidental dislocation of the pessary from or within the vaginal cavity. Generally, the pressure of an inflated posterior chamber will vary from 0.1 to 5.0 atmospheres greater than ambient air pressure, and preferably 0.10 to 3.0 atmospheres. Generally, an inflated anterior chamber pressure will vary from about 1 to 2.5 times that disclosed for a posterior chamber. In treating UI a greater anterior chamber pressure, compared to the posterior chamber pressure, will generally be required. Generally, posterior chambers inflate to a maximum volume 50% to 500% greater than their deflated volume. The maximum inflated volume of a posterior chamber will vary from about 40 cc for a small chamber (child) to 500 cc for a large chamber (large adult), preferably from 60 cc to 200 cc and most preferably from 80 cc to 120 cc. The anterior chamber is preferably adapted to snugly fit in the vestibule. Generally, anterior chambers inflate to a maximum volume 0% to 100% greater than their deflated volume. The maximum inflated volume of an anterior chamber will vary from about 10 cc for a small chamber to 150 cc for a large chamber, preferably from about 30 to 100 cc and most preferably from about 40 to 90 cc. The posterior chamber is preferably adapted to fit the fornix. However, there need not be an exact correspondence between the functional (anterior and posterior) chambers of the device and these anatomical descriptions (which indeed do not describe a sharp anatomical change, but rather a gradual one). Thus the anterior chamber of a pessary of the invention can extend into the fornix region or the anchor member (posterior chamber) can extend into the vestibule region, as long as the other essential features of the invention are present in the device.

Figure 2:
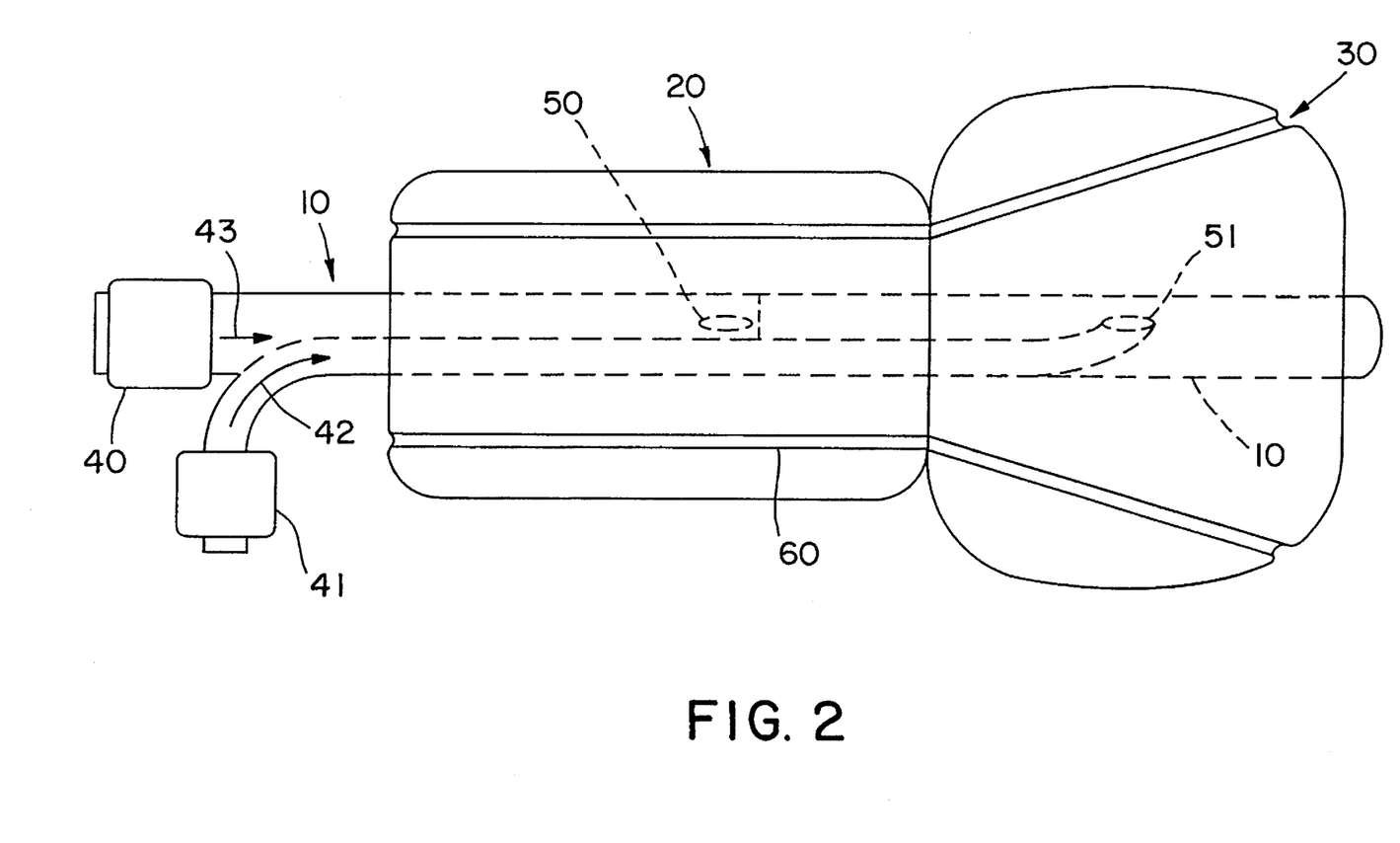
FIG. 2 is a plan view of one embodiment of the vaginal pessary.

In some embodiments an inflation channel is provided for fluid connections between chambers and inflation valves. In such embodiments at least one inflatable chamber is attached and fluidly connected to an inflation channel with an inflation valve. "Fluidly connected" refers herein to a connection that permits the passage of a fluid such as (but not limited to) air or water between a chamber and an inflation valve located outside the body cavity when the device is properly inserted. Chambers can be inflated through the inflation channel sequentially, in parallel or independently. Independent inflation (separate inflation) of chambers is preferred for two-chambered devices. If more than two chambers are used, it is preferred to inflate chambers located in the anterior region of the vagina independently from chambers located in the posterior region of the vagina. FIG. 2 shows independently inflatable anterior and posterior chambers (20 and 30, respectively). Each chamber is independently inflatable using inflation channel 10. To accomplish independent inflation, a first inflation valve 40 is fluidly connected to a first inflation opening 50 located inside the anterior inflatable chamber 20; a second inflation valve 41 is fluidly connected to a second inflation opening 51 located inside the posterior chamber. Arrow 43 indicates inward fluid flow in a first tube fluidly connecting a first inflation valve 40 with anterior chamber 20. Arrow 42 indicates inward fluid flow in a second tube fluidly connecting a second inflation valve 41 to the posterior chamber.

FIG. 3 shows an inflatable anterior chamber and a non-inflatable posterior member (20 and 70, respectively). The anterior chamber is inflated using inflation channel 10. A first inflation valve 40 is fluidly connected to a first inflation opening 50 located inside the anterior inflatable chamber 20. Arrow 43 indicates inward fluid flow in a first tube fluidly connecting a first inflation valve 40 with anterior chamber 20.

Separate inflation of the anterior and posterior chambers permits each chamber to be individually and snugly fit to two different regions of the vaginal cavity. Thus, the posterior chamber can be inflated to a radius of sufficient size to anchor the device in the posterior region of the vagina, and the anterior chamber can be separately inflated to control incontinence and separately deflated to permit urination. The inflated diameter (or similar cross sectional dimension) of the posterior chamber is not necessarily larger than (or even as large as) the anterior chamber. For instance, if the posterior chamber is partially inflated, yet firmly held in place, the anterior chamber's fully inflated diameter may be greater to achieve complete compression of the urethra lumen. Preferably, the anterior chamber has a fully inflated diameter less than or equal to the fully inflated diameter of the anchoring chamber. When the anterior chamber is properly inflated it prevents urinary leakage by exerting sufficient pressure against the vaginal wall in the vestibule to compress the urethra.

The sizes of each chamber can vary greatly depending on the dimensions of the vaginal cavity of the user. Preferably, the anterior chamber will be 3 to 7 cm in length, preferably 4.0, 5.6 or 6.0 cm in length, as measured along the longitudinal axis of the inflation tube. The fully inflated cross-sectional dimension (diameter) of the anterior chamber can range from 0.5 to 6 cm across, and is preferably, 4.0 to 5.0 cm across. The posterior chamber can range from 0.5 to 4 cm in length, and is preferably 2.0 to 3.0 cm in length. The fully inflated cross sectional dimension (diameter) of the posterior chamber can range from 0.5 to 10 cm across, and preferably, 3.0 to 6.0 cm across. If multiple chambers are used in either the fornix or the vestibule, the aggregate lengths, cross sectional dimensions and volumes of those chambers should approximate the lengths, cross sectional dimensions and volumes disclosed for posterior and anterior chambers, respectively, of the two-chambered pessary.

The shapes of the chamber can vary greatly depending on the contours of the vaginal wall anatomy and application (for example, simple incontinence versus vaginal prolapse). The chambers can be adapted to fit the vaginal cavity by using a shape that can be, but is not limited to, one or a combination of the following shapes: cylinder, discus, sphere, rectangle, dumbbell and ellipse. Preferably, the anterior chamber is shaped like a cylinder or ellipse. Variance in user anatomy may require compression of a specific area of the urethra in which case the anterior chamber can also have surface protrusions, solid or inflatable, on a surface of an inflatable chamber. Protrusions provide a more focused pressure point when the chamber is inflated. If the posterior chamber is formed as a discus or dumbbell, preferably the longest dimension of the posterior chamber is perpendicular to the longitudinal axis of the pessary. It will be recognized that the manufactured shapes are not likely to be exactly those of the geometrical shapes but will be approximate and are likely to have rounded edges.

For some devices, particularly those used in a reusable fashion (where the device remains inserted in the vagina for days and can be reused), the device preferably has a means for draining the vagina of vaginal secretions, such as a channel leading through the chambers to the outside of the body cavity. Preferably, the anterior and posterior chambers have a drainage surface groove or grooves 70 to allow for drainage of vaginal secretions. These grooves are preferably located on the dorsal side (the side closer to the vertebrae) of the device when inserted in its normal manner.

The inflation channel, when present, provides at least one fluid connection that connects at least one chamber to a corresponding inflation valve. The fluid connections are typically in the form of a tube or other form of independent fluid passageway. Thus the fluid connections are often referred to herein as "inflation tubes," even though the fluid connection is not necessarily in the shape of a tube. The "tube" thus represents whatever shape is present to connect the chamber to the valve and may merely be the end of the chamber itself (e.g., for the anterior chamber that is adjacent to the external opening of the vagina) or an extension thereof. Fluid connections separately connecting each inflation valve to each chamber are preferred. The individual fluid connections can be bundled in the inflation channel. One or more openings in the inflation channel allow individual fluid connections to be made to the individual chambers. One end, referred to as the "first end," of each fluid connection is fluidly connected to a chamber. An inflation valve, when a valve is used, is attached to the second end of the fluid connection. The second end is anterior to the first end when the device is inserted into the vagina, and the second end and/or valve is normally located outside the vagina when the pessary is in use. In view of the broad meaning of inflation tube, it should be apparent that the two "ends" of the inflation tube may merely be the two sides of the chamber/valve junction if the valve is directly attached to a chamber, as occurs is some embodiments.

The inflation channel in some embodiments also acts as a base or support for a chamber or chambers. In such cases the inflation channel is manufactured to provide sufficient axial rigidity to permit convenient and slidable insertion of the pessary into the vagina. Each chamber is attached at a site on the longitudinal axis of the inflation channel that corresponds to the correct anatomical regions of the vagina when the device is inserted into the vagina. Inflatable chambers can be attached to the inflation channel in a molded fashion or using an adhesive, such as a silicone adhesive.

A chamber can be attached to the inflation channel on one or more sides of the inflation channel. A chamber is preferably attached radially to the inflation channel to minimize contact of the inflation channel with the walls of the vagina. Preferably a chamber is symmetrically and radially attached to the inflation channel. More preferably a chamber surrounds the inflation channel along its longitudinal axis and is contiguously attached to the inflation channel. Contiguously attached as used herein means attached without interruptions. When a cylindrical shape is used for a chamber, the chamber is preferably attached contiguously to the inflation channel at the ends of the cylinder to help maintain the cylindrical shape when in use.

Fluid connections need not take place through a central inflation channel as shown in the embodiment of FIG. 1; instead they can be entirely separate from each other if desired. In such cases the function of the central inflation channel as a support member for providing rigidity to allow ease of insertion of the pessary can be provided by a support member that does not make any fluid connections. Alternatively, a central support member is not required in some embodiments if other means are provided for inserting the pessary into the vagina. For example, a disposable sheath or other insertion device (such as those commonly used in the tampon art) can be used with an un-inflated/un-expanded pessary, followed by inflation or expansion of the anchor member after removal of the insertion device.

In the two-chamber embodiment, chambers are preferably separated according to the dimensions of the vagina in which the device will be used. The larger the separation between vestibule and the fornix, the larger the separation between the two chambers for a comfortable fit. However, no separation is necessary between the two chambers. Preferably the separation distance along the longitudinal axis of the inflation channel is less than 1 cm, but could be as great as 2 to 3 cm or longer.

The inflation channel is designed according to the type of chamber inflation that is desired, such as parallel or separate inflation, as discussed herein. If two chambers are used with separate inflation, the inflation channel is preferably made of a support tube adapted to provide attachment sites for the anterior chamber and the posterior chamber, a first inflation tube fluidly connected to the anterior chamber and adapted to fit inside the support tube, and a second inflation tube fluidly connected to the posterior chamber and adapted to fit inside the support tube.

The diameter of an inflation channel will vary according to the size of the user. Generally, the outside diameter of the inflation channel will vary from about 0.4 cm to 2.0 cm, and preferably from about 0.8 to 1.5 cm. The internal diameter of an inflation tube will generally vary from about 0.1 cm to 1 cm, and preferably from about 0.2 to 0.6 cm. Alternatively, the inflation channel can be configured as a tube having two separate channels separately and fluidly connected to the anterior and posterior chambers. In this embodiment it is preferred that the two channels of the tube are formed in one molded piece.

In preferred embodiments, each inflation tube is connected to an inflation valve to permit inflation of the chambers. The inflation valve comprises at least one valve that controls the passage of fluid into a chamber or chambers. Preferably, two valves are used, a first valve to control fluid flow through a first inflation tube to the anterior chamber and a second valve to control fluid flow through a second inflation tube to the posterior chamber. To maximize comfort and ease of operation, the first and second valves are preferably located outside the body cavity when the pessary is placed inside the vaginal cavity. To further make the valves easy to manipulate, especially for patients with compromised manual dexterity, the valves are preferably coded by feel (such as texture, size, or shape). The valves can also be coded by lettering or color, or by any combination of coding types. Valves can be attached to the inflation tubes by methods known in the art, such as adhesive or molding.

The valves used to control fluid flow should preferably be easy to operate, preferably by the fingers of the user. Many such valves are known in the art, for example, Luer lock valves, one-way fluid valves, or Foley catheter valves. To allow for inflation, the valves are compatible with a fluid pump as known in the art, such as a syringe, a one-way air valve pump, a basketball shoe pump, a compressed air canister, a compressible fluid reservoir (such as compressible rubber bladder that engages with the valve) or a piston pump. The pumps can be made an integral part of the pessary or can be separate, as described below in more detail.

The pessary can be made either for reuse or disposal after a single or limited number of uses. Disposable pessaries are preferably disposed after 1 to 14 days, more preferably after 1–7 days, and most preferably after 1–2 days. Both reusable and disposable pessaries are generally worn for 1 to 36 hours, preferably not longer than 12 to 15 hours. A pessary is generally washed (e.g., with soap and water) after use and before re-insertion.

The pessary can be made of a variety of biocompatible materials, i.e., a material that minimizes the reaction of the body resulting from contact of the material with the vaginal wall and provides for a comfortable feel and fit by the user. The manner in which the device is intended to be used, whether reusable or disposable, will determine in part what type of material is preferred. Vaginal pessaries that are reused are preferably made from material that is more resistant to degradation by mechanical movement, bodily fluids, cleaning procedures, and oxidation than disposable vaginal pessaries. If the vaginal pessary is used with a lubricant to ease insertion, the biocompatible material should be compatible with that lubricant.

Various biocompatible materials can be used, for chambers or other members, such as silicone (for instance, silicone elastomers, such as poly-dimethyl siloxane), latex, polyurethane, polyethylene, balloon angioplasty materials, Silastic™, and teflon-coated latex. The biocompatible material used for a chamber can be an elastic material or a non-elastic, flexible material. A non-elastic, flexible material provides for a maximum, inflated cross sectional dimension (such as diameter) of the chamber. In order to provide for maximum comfort and incontinence control, each chamber can be made of a different biocompatible material or different regions of a chamber can be made of a different biocompatible material. For example, the anterior chamber can be made of a non-elastic, or less distensible, flexible material appropriately sized for urethra compression when inflated and the anchoring chamber can be made of a elastic material that can inflate to a more variable range of sizes inside the fornix region of the vagina to provide for a secure fit when encountering different abdominal pressures when the user stands or lies down.

The inflation channel is also made of a biocompatible material. Suitable materials for the inflation channel include silicone (for instance, silicone elastomers, such as poly-dimethyl siloxane (but stiffer than that used for chambers)), latex, polypropylene, polyethylene, and Teflon™ coated latex. As discussed herein the inflation channel (or other central member) is flexible to conform to the shape of the vaginal cavity while being rigid enough to provide support for the chambers and to direct the insertion of the device into the vagina. It will also be appropriate in various embodiments for the tip of the inflation channel to be made as a solid tip to aid insertion of the device into the vagina. The inflation channel can be made of different materials in its different component parts to maximize the comfort of the user while wearing the device. For instance, the portion of the inflation channel that extends past the vaginal cavity can be made more flexible and less rigid than the material used for the portion of the inflation channel inside the vaginal cavity. This permits the portion of the inflation channel outside the body to be more easily stored.

The invention also includes a method of treating incontinence in a female human. To treat incontinence, a pessary of the invention is inserted into the vagina. Preferably the pessary is adapted so that the pessary can be inserted in a tampon-like fashion. At least one chamber is adapted to snugly fit in a vaginal cavity. To control incontinence at least one inflatable chamber is inflated with sufficient pressure to compress the urethra and prevent the flow of urine. To anchor the pessary in the vagina at least one posterior chamber is inflated or inserted (i.e., in the diaphragm embodiment). If the method is used with a non-inflatable chamber, it is preferable to use a non-inflatable chamber similar in shape and dimensions to a contraceptive diaphragm. If the users require day-to-day vaginal care it is preferable to use disposable pessaries.

The invention also includes a method of treating cystoceles, rectoceles, uterine prolapse or vaginal prolapse in a female human. To treat these medical conditions a pessary of the invention is inserted into the vagina. At least one chamber of the device is inflated to prevent tissue intrusion into the vagina. To treat uterine prolapse a larger inflatable posterior chamber, compared to that used to treat incontinence, will help prevent the intrusion of uterus into the vagina. Generally, the posterior chamber may require a large diameter in order to treat a cystocele, rectocele or uterine prolapse.

The invention also includes a kit comprising a pessary and a fluid pump adapted to the inflation valve (or valves) used to inflate and deflate the pessary. The components of the kit are typically provided in a container that can be adapted to hold the individual components The kit can further include a biological lubricant, such as K-Y jelly.

The invention now being fully described, it will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

I claim:

1. A pessary device comprising:
   (a) an inflatable, anterior chamber adapted to fit in a vestibule of a vaginal cavity of a human when inflated, wherein said inflatable anterior chamber compresses a urethra of the human when inflated,
   (b) a first inflation tube having a first end fluidly connected to said inflatable, anterior chamber and a second end having a first inflation valve that permits inflation and deflation of said inflatable anterior chamber,
   (c) an anchor member comprising an inflatable, posterior chamber adapted to snugly fit in a posterior region of the vaginal cavity when inflated, said inflatable posterior member being posteriorly connected to said inflatable anterior chamber when said pessary device is in its normal operating position, and
   (d) a second inflation tube having a first end fluidly connected to said inflatable posterior chamber and a second end having a second inflation valve that permits inflation and deflation of said inflatable posterior chamber;
   wherein inflation and deflation of said inflatable posterior and anterior chambers are separately controlled.

2. The pessary device of claim 1, wherein said inflatable anterior chamber has a fully inflated diameter less than or equal to a fully inflated diameter of said inflatable, posterior chamber.

3. The pessary device of claim 1, wherein said inflatable posterior chamber contains an expandable material.

4. The pessary device of claim 1, wherein said pessary comprises a central support member and said inflatable anterior and posterior chambers circumscribe and are contiguously attached to said central support member.

5. The pessary device of claim 4, wherein said support member forms an inflation channel comprising a support tube adapted to provide attachment sites for said inflatable anterior chamber and said inflatable posterior chamber; said first inflation tube fluidly connected to said inflatable anterior chamber and adapted to fit inside said support tube; and said second inflation tube fluidly connected to said inflatable posterior chamber and adapted to fit inside said support tube.

6. The pessary device of claim 4, wherein said support member comprises a tube having two separate channels molded together, each of said channels separately and fluidly connected to one or another of said inflatable anterior and posterior chambers.

7. The device of claim 1, wherein said first and second inflation valves are Luer lock valves.

8. The pessary device of claim 1, wherein said first and second inflation valves have different tactile coding.

9. The pessary device of claim 1, wherein said pessary device has at least one drainage surface groove on said inflatable anterior chamber and said inflatable posterior chamber to allow for drainage of vaginal secretions on an external surface of said pessary device.

10. The pessary device of claim 1, wherein said first and second inflation valves each comprises a fluid-pump-compatible valve.

11. The pessary device of claim 10, wherein said fluid-pump-compatible valve is selected from the group consisting of a syringe valve, a one-way valve air pump valve, a compressed air canister valve, a fluid bladder valve and a piston pump valve.

12. The pessary device of claim 1, wherein said inflatable anterior and posterior chambers are made of an elastic material or a non-elastic, flexible material.

13. The pessary device of claim 12, wherein said inflatable anterior and posterior chambers are made of a material selected from the group consisting of silicone, latex, polyurethane, polyethylene and polytetrafluoroethylene-coated latex.

14. The pessary device of claim 12, wherein said inflatable anterior and posterior chambers are made of different materials.

15. A kit, comprising:
    the pessary device of claim 1,
    a fluid pump adapted to fit the inflation valve of said pessary device, and
    a container adapted to contain said pessary device and said fluid pump.

16. The kit of claim 15 further comprising a biocompatible lubricant.

17. A method of treating incontinence in a female human with a urethra, comprising:
    inserting the pessary device of claim 1 into a vagina of said human, inflating the posterior inflatable chamber sufficiently to fit in a posterior region of a vaginal cavity, and
    inflating said inflatable anterior chamber of said pessary device sufficiently to compress the urethra of said human and prevent urine flow.

18. The method of claim 17, further comprising deflating said inflatable anterior chamber to allow said human to urinate and re-inflating said inflatable anterior chamber after urination.

19. A method of treating cystoceles, rectoceles, uterine prolapse or vaginal prolapse in a vagina of a human, comprising:
    inserting a pessary of claim 1 into the vagina of said human, inflating the posterior inflatable chamber sufficiently to fit in a posterior region of a vaginal cavity, and
    inflating the chamber of said pessary to prevent tissue intrusion into the vagina.

* * * * *

UNITED STATES PATENT AND TRADEMARK OFFICE
CERTIFICATE OF CORRECTION

PATENT NO. : 5,603,685
DATED : February 18, 1997
INVENTOR(S) : Ronald F. Tutrone, Jr., M.D.

It is certified that error appears in the above-indentified patent and that said Letters Patent is hereby corrected as shown below:

Title page, item [76], inventor: Delete "Donald" and replace with-- Ronald--.

Signed and Sealed this

Third Day of June, 1997

*Attest:*

BRUCE LEHMAN

*Attesting Officer*  Commissioner of Patents and Trademarks